(12) United States Patent
Bille

(10) Patent No.: US 7,101,364 B2
(45) Date of Patent: *Sep. 5, 2006

(54) METHOD AND APPARATUS FOR INTRASTROMAL REFRACTIVE SURGERY

(75) Inventor: Josef Bille, Heidelberg (DE)

(73) Assignee: 20/10 Perfect Vision Optische Geraete GmbH, Heidelberg (DE)

( * ) Notice: Subject to any disclaimer, the term of this patent is extended or adjusted under 35 U.S.C. 154(b) by 60 days.

This patent is subject to a terminal disclaimer.

(21) Appl. No.: 10/429,232

(22) Filed: May 2, 2003

(65) Prior Publication Data

US 2003/0229339 A1 Dec. 11, 2003

Related U.S. Application Data

(63) Continuation-in-part of application No. 09/976,177, filed on Oct. 12, 2001, now Pat. No. 6,610,051.

(51) Int. Cl.
A61F 9/08 (2006.01)

(52) U.S. Cl. ............................................ 606/5; 606/10

(58) Field of Classification Search .................... 606/3, 606/5, 10–14; 351/206–212
See application file for complete search history.

(56) References Cited

U.S. PATENT DOCUMENTS

| 4,309,998 A | 1/1982 | Aron nee Rosa et al. |
| 4,391,275 A | 7/1983 | Fankhauser et al. |
| 4,538,608 A | 9/1985 | L'Esperance, Jr. |
| 4,601,288 A | 7/1986 | Myers |
| 4,633,866 A | 1/1987 | Peyman |
| 4,665,913 A * | 5/1987 | L'Esperance, Jr. ............. 606/3 |
| 4,669,466 A | 6/1987 | L'Esperance |
| 4,718,418 A | 1/1988 | L'Esperance, Jr. |
| 4,721,379 A | 1/1988 | L'Esperance |
| 4,732,148 A | 3/1988 | L'Esperance, Jr. |
| 4,770,172 A | 9/1988 | L'Esperance, Jr. |
| 4,907,586 A * | 3/1990 | Bille et al. ...................... 606/5 |
| 4,988,348 A | 1/1991 | Bille |
| 5,062,702 A | 11/1991 | Bille |
| 5,246,435 A | 9/1993 | Bille et al. |
| 5,439,462 A | 8/1995 | Bille et al. |
| 5,984,916 A | 11/1999 | Lai |
| 5,993,438 A * | 11/1999 | Juhasz et al. .................. 606/5 |
| 6,110,166 A | 8/2000 | Juhasz |
| 6,146,375 A | 11/2000 | Juhasz et al. |
| 6,155,684 A * | 12/2000 | Bille et al. ................... 351/212 |

(Continued)

FOREIGN PATENT DOCUMENTS

EP 1302186 A2 4/2003

(Continued)

Primary Examiner—David M. Shay
(74) Attorney, Agent, or Firm—Nydegger & Associates

(57) ABSTRACT

A method and apparatus for intrastromal refractive surgery is disclosed wherein tissue at selected locations within the stroma of the cornea is photoablated using a pulsed laser beam. The apparatus includes an optical system for forming a shaped laser beam having a waist at a predetermined distance from the optical system. The pulse duration and pulse energy of the laser beam are selected to cause ablation to occur in front of the waist (i.e. between the waist and the optical system). To achieve this, a pulse energy is used that exceeds the minimum pulse energy required for ablation at the waist. By ablating in front of the waist, a relatively large ablation zone (per pulse) is created (compared to ablation at the waist). Furthermore, while the laser is scanned through the cornea to effectuate a refractive change, the optical system maintains a uniform waist for the laser beam.

3 Claims, 3 Drawing Sheets

U.S. PATENT DOCUMENTS

| | | |
|---|---|---|
| 6,325,792 B1 | 12/2001 | Swinger et al. |
| 6,428,533 B1 * | 8/2002 | Bille .......................... 606/11 |
| 6,451,006 B1 | 9/2002 | Bille |
| 6,610,051 B1 * | 8/2003 | Bille ............................ 606/5 |
| 2001/0010003 A1 | 7/2001 | Lai |
| 2002/0193704 A1 | 12/2002 | Goldstein et al. |
| 2003/0003295 A1 | 1/2003 | Dreher et al. |
| 2003/0014042 A1 | 1/2003 | Juhasz et al. |

FOREIGN PATENT DOCUMENTS

| | | |
|---|---|---|
| EP | 1316298 A2 | 6/2003 |

* cited by examiner

METHOD AND APPARATUS FOR INTRASTROMAL REFRACTIVE SURGERY

This application is a continuation-in-part of Application Ser. No. 09/976,177 filed Oct. 12, 2001, now U.S. Pat. No.6,610,051. The contents of Application Ser. No. 09/976,177 are incorporated herein by reference.

FIELD OF THE INVENTION

The present invention pertains generally to ophthalmic laser surgery procedures. More particularly, the present invention pertains to laser surgical procedures which are performed to reshape or restructure the cornea of an eye by using photoablation techniques to remove stromal tissue. The present invention is particularly, but not exclusively, useful as a method and system for quickly altering the refractive properties of a cornea with little or no heat damage to non-target corneal tissue.

BACKGROUND OF THE INVENTION

It is well known that the refractive properties of the cornea can be altered by the selective removal of corneal tissue. For example, a myopic condition of the eye can be corrected by selectively removing corneal tissue from the central portion of the cornea. Similarly, a hyperopic condition can be corrected by selectively removing corneal tissue within a peripheral ring surrounding the central portion of the cornea.

With this in mind, a general knowledge of the anatomy of the cornea is helpful to appreciate the problems that must be confronted during refractive corrections of the cornea. In detail, the cornea comprises various layers of tissue which are structurally distinct. In order, going, in a posterior direction from outside the eye toward the inside of the eye, the various layers in a cornea are: an epithelial layer, Bowman's membrane, the stroma, Descemet's membrane, and an endothelial layer. Of these various structures, the stroma is the most extensive and is generally around four hundred microns thick. Additionally, the healing response of the stromal tissue is generally quicker than the other corneal layers. For these reasons, stromal tissue is generally selected for removal in refractive correction procedures.

In greater detail, the stroma of the eye is comprised of around two hundred identifiable and distinguishable layers of lamellae. Each of these layers of lamellae in the stroma is generally dome-shaped, like the cornea itself, and they each extend across a circular area having a diameter of approximately nine millimeters. Unlike the layer that a particular lamella is in, each lamella extends through a shorter distance of only about one tenth of a millimeter (0.1 mm) to one and one half millimeters (1.5 mm). Thus, each layer includes several lamellae. Importantly, each lamella includes many fibrils which, within the lamella, are substantially parallel to each other. The fibrils in one lamella, however, are not generally parallel to the fibrils in other lamellae. This is so between lamellae in the same layer, as well as between lamellae in different layers. Finally, it is to be noted that, in a direction perpendicular to the layer, each individual lamella is only about two microns thick.

One technique for altering the refractive properties of the cornea involves the use of a pulsed laser beam to photoablate stromal tissue. In this technique, a pulsed laser is focused beneath the anterior surface of the cornea to photoablate tissue within the stroma. Heretofore, it has been suggested that the optimal photoablation of tissue with minimal side effects can be obtained using a laser beam having a pulse duration of 100 femtosecond (fs) focused to an ablation spot size of approximately 10 µm with a pulse energy approximately equal to the ablation energy threshold. However, with these parameters, a typical refractive procedure (e.g. a procedure involving the ablation of an area having an approximate diameter of 6.5 mm) would require an undesirably long scan time. Specifically, a single pass of the laser beam over an area this size may require approximately 400,000 pulses, and further, the corrective procedure may require several passes. Thus, for a typical laser beam having a pulse repetition frequency of approximately 10 KHz, each pass would take almost 40 seconds.

It is to be appreciated that procedures requiring a lengthy scan time (e.g. 40 seconds or more) can pose a number of serious problems. One such problem involves the movement of the eye during a scan. To overcome eye movement, eye restraint is often used. Unfortunately, restraining the eye is only somewhat effective and long periods of eye restraint can cause serious discomfort for the patient. In addition to eye movement, patient blinking is another factor that must be considered during a corneal laser procedure. Each time a patient blinks, a new tear film is deposited on the anterior surface of the cornea. Each tear film affects the optical path of the laser beam in a slightly different manner, affecting the precision of the operation. Thus, it is preferable to perform an entire laser scan with a single tear film, if possible. Typically, 10 seconds is about the maximum time that a patient can restrain from blinking, thus it is preferable to complete an entire laser scan in less than about 10 seconds.

In addition to requiring an unacceptably long laser scan, operating at or near the ablation energy threshold has other drawbacks. Specifically, operating at or near the ablation energy threshold is non-optimal because statistical fluctuations of the tissue ablation process are more pronounced (compared with ablation at energies significantly above threshold) leading to ablation non-uniformities. These ablation non-uniformities, in turn, can create undesirable refractive inhomogeneities.

In all surgical procedures, damage to non-target tissue is to be avoided. During photoablation of target tissue, nearby (non-target) tissue is heated. Although some heating of non-target tissue can be accommodated without damage, excessive heat must be avoided. In greater detail, for stromal tissue, a temperature rise of about 3° C. can be tolerated without long-term cell damage. In contrast, temperature increases of between about 8° C. and 23° C. can result in tissue shrinkage, cell denaturation, loss of cell function and coagulation.

During photoablation, a series of gas bubbles are formed as the laser beam is scanned through the stroma. If the ablation sites are created too closely together and the bubbles are large, the bubbles may overlap. Typically, it is this overlap that is responsible for most of the heat damage to non-target tissue. Generally, ablation using a relatively large pulse energy results in a relatively large bubble, and conversely, ablation using a relatively small pulse energy results in a relatively small bubble. With this in mind, one way to prevent bubble overlap and its associated heat damage is to use relatively low pulse energies to create relatively small bubbles. However, as indicated above, relatively low pulse energies can lead to ablation nonuniformities and unacceptably long procedure times.

In light of the above, it is an object of the present invention to provide methods and apparatuses suitable for photoablating a relatively large amount of targeted stromal tissue in a relatively short scan time without heating non-target tissue to harmful temperatures. It is yet another object of the present invention to provide methods and apparatuses for photoablating stromal tissue at pulse energies sufficient to prevent non-uniform ablation and with little or no adverse side effects. Another object of the present invention is to provide stable and efficient methods and apparatuses for photoablating stromal tissue. Yet another object of the present invention is to provide methods and apparatuses for changing the refractive properties of a cornea which are easy to use, relatively simple to implement, and comparatively cost effective.

SUMMARY OF THE INVENTION

The present invention is directed to methods and apparatuses for intrastromal refractive surgery wherein tissue at selected locations within the stroma of the cornea is photoablated using a pulsed laser beam. For the present invention, the apparatus includes an optical system for forming a shaped laser beam having a waist at a predetermined distance from the optical system. For typical applications, a laser beam having a waist diameter, $D_{WAIST}$, of about 10 μm is used. In one embodiment of the present invention, adaptive-optical beam shaping is used to establish and maintain a uniform beam waist as the laser beam is scanned to various locations within the stroma. Specifically, as detailed further below, wavefront analysis can be used to drive an active mirror, which in turn, shapes the laser beam to maintain a uniform beam waist as the laser beam is scanned through the stroma.

For the present invention, the pulse duration and pulse energy of the laser beam are selected and controlled to cause ablation to occur in front of the waist (i.e. between the waist and the optical system). As implied above, the ablation energy threshold for stromal tissue is a function of both the pulse duration and the diameter of the ablation zone. Accordingly, for a given pulse duration and waist diameter, $D_{WAIST}$, the minimum pulse energy required to ablate tissue at the waist can be determined. However, for the present invention, a laser beam having a pulse energy greater than the minimum pulse energy required for ablation at the waist is used, and accordingly, ablation occurs at a location in front of the waist. By ablating in front of the waist, a larger ablation zone (per pulse) can be obtained as compared to procedures designed to ablate tissue at the waist.

In one embodiment of the present invention, a laser beam having pulse durations of approximately 600 fs is shaped to establish a waist having a diameter of approximately 10 μm. Also for this embodiment, a pulse energy of approximately 6 μJ is used (approximately 3 times the pulse energy required to ablate tissue at the 10 μm waist) creating an ablation zone having an approximate diameter of 15–20μm that is located about 50 μm in front of the waist. Accordingly, for this embodiment, the laser beam is shaped and directed to interpose the target tissue on a beam path between the optical system and the waist, with the waist positioned about 50 μm from the target tissue.

In another aspect of the present invention, the laser beam is partitioned into a plurality of spaced-apart beams (e.g. seven spaced-apart beams) with each spaced-apart beam shaped to establish a respective beam waist as described above. By partitioning the beam, a plurality of spaced-apart ablation zones can be simultaneously created. Specifically, for each spaced-apart beam, an ablation zone is created on a respective beam path between the respective beam waist and the optical system. The spaced-apart beams are then scanned together as a group through the stroma to photoablate a pre-selected pattern of tissue. This allows a large amount of stromal tissue to be ablated quickly while minimizing heat damage to non-target stromal tissue.

Further, this technique allows the spacing between ablation zones to be adjusted in relation to the corneal location where tissue is being ablated. More specifically, for ablation of tissue near the center of the cornea where heat dissipation is relatively slow (i.e. tissue near the optical axis of the eye), a relatively large spacing between ablation zones within the group of spaced-apart beams can be used to minimize heat damage. On the other hand, for ablation of tissue near the periphery of the cornea where heat dissipation is relatively fast, a relatively small spacing between ablation zones within the group of spaced-apart beams can be used.

In another embodiment of the present invention, the laser beam is scanned along two interlaced, spiral paths to minimize heat damage to non-target tissue. For example, in one implementation, the pulsed, shaped laser beam is first scanned outwardly from the corneal center and toward the corneal periphery on a first spiral path. Thereafter, the pulsed, shaped laser beam is scanned inwardly in a direction from the corneal periphery and toward the corneal center on a second spiral path.

BRIEF DESCRIPTION OF THE DRAWINGS

The novel features of this invention, as well as the invention itself, both as to its structure and its operation, will be best understood from the accompanying drawings, taken in conjunction with the accompanying description, in which similar reference characters refer to similar parts, and in which.

DESCRIPTION OF THE PREFERRED EMBODIMENTS

Figure 1:
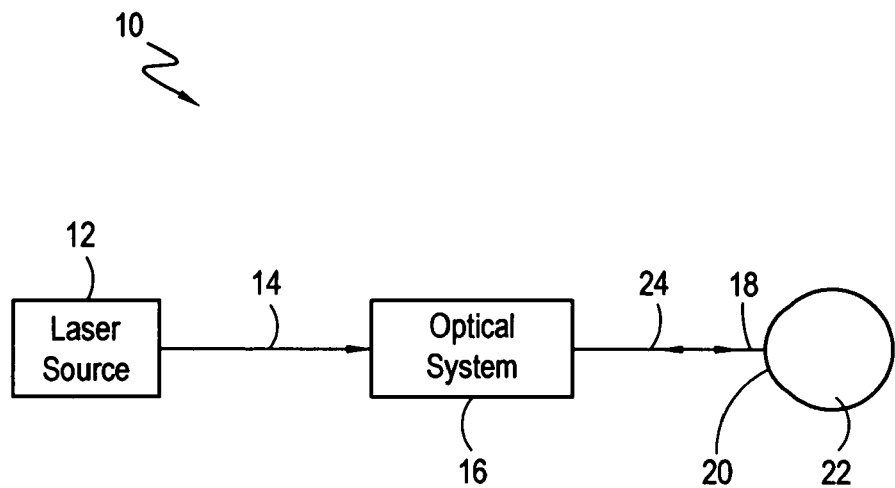
FIG. 1 is a simplified, schematic diagram of an apparatus for performing intrastromal refractive surgery using a pulsed laser beam.

Referring initially to FIG. 1, an apparatus for intrastromal refractive surgery is shown schematically and is generally designated 10. As shown, the apparatus 10 includes a laser source 12 which, preferably, is capable of generating and controlling a source beam 14 having a continuous train of laser pulses of substantially constant pulse duration and pulse energy. In one embodiment of the apparatus 10, a source beam 14 having a pulse duration of approximately 600 fs and pulse energy of approximately 6 µJ is generated by the laser source 12.

Continuing with FIG. 1, it can be seen that the apparatus 10 further includes an optical system 16 for forming a shaped laser beam 18 and directing the shaped laser beam 18 toward and into the cornea 20 of an eye 22. Also shown in FIG. 1, reflected light 24 from the eye 22 can be received by the optical system 16. As further detailed below, analysis of the reflected light 24 is useful for several reasons including, but not limited to, applications in which the tissue targeted for ablation lies inside a lamella and in applications in which the tissue targeted for ablation lies on an interface between layers of lamellae. One such application in which the tissue targeted for ablation lies on an interface between layers of lamellae is the creation of a corneal flap for a LASIK type procedure (see detailed discussion below).

Figure 2:
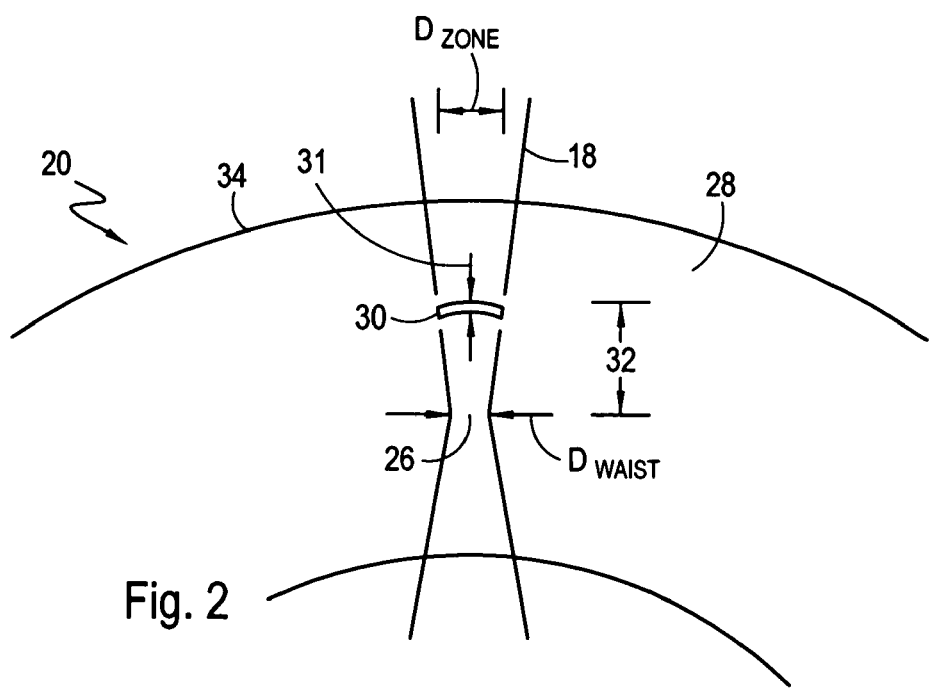
FIG. 2 is a schematic, not to scale, view of a section through the cornea showing the ablation of stromal tissue by a shaped, pulsed laser beam generated using the apparatus of FIG. 1.

As best seen in FIG. 2, the shaped laser beam 18 is formed with a waist 26 by the optical system 16 (see FIG. 1). Also shown in FIG. 2, the waist 26 defines a waist diameter, $D_{WAIST}$. Continuing now with cross-reference to FIGS. 1 and 2, it can be seen that the pulse duration and pulse energy of the shaped laser beam 18 can be selected by the operator (and controlled by the laser source 12) to cause ablation to occur in front of the waist 26 and within the stroma 28 of the cornea 20. Specifically, once the pulse duration has been selected and the waist diameter, $D_{WAIST}$ defined, the pulse energy is chosen to exceed the ablation energy threshold for stromal tissue at the waist 26. The result is the creation of an ablation zone 30 that is positioned between the waist 26 and the optical system 16.

In one application of the apparatus 10, a source beam 14 having pulses of approximately 600 fs duration and a pulse energy of approximately 6 µJ is generated by the laser source 12. The source beam 14 is then shaped by the optical system 16 to form a shaped, pulsed laser beam 18 having a waist diameter, $D_{WAIST}$ of approximately 10 µm. With these parameters, an ablation zone 30 having an approximate diameter $D_{ZONE}$ of approximately 15–20 µm and an ablation depth 31 per pulse of approximately 2 µm (4 µm peak ablation value) is created. As further shown, the ablation zone 30 is located at a distance 32 of approximately 50 µm from the waist 26. For example, to photoablate target tissue located approximately 180 µm from the anterior surface 34 of the cornea 20, the shaped laser beam 18 can be directed to position the waist 26 at approximately 230 µm from the anterior surface 34 to interpose the target tissue on a beam path between the optical system 16 and the waist 26. With these laser parameters (i.e. 600 fs pulse duration and 6 µJ pulse energy) the pulse energy is approximately three times the ablation energy threshold for ablation at a waist 26 having a diameter, $D_{WAIST}$ Of 10 µm.

Figure 3:
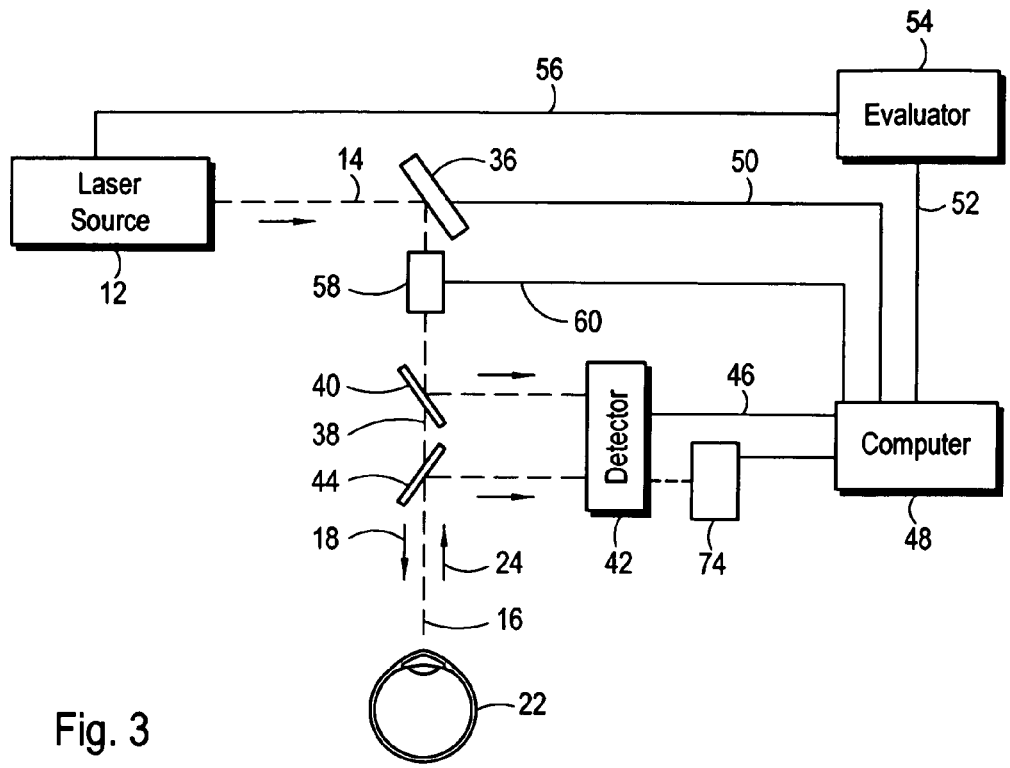
FIG. 3 is a schematic diagram of an embodiment of the apparatus shown in FIG. 1 showing components of a typical optical system in an exemplary arrangement.

The components of one embodiment of the apparatus 10 can be appreciated with reference to FIG. 3. Specifically, FIG. 3 shows an embodiment wherein adaptive-optical beam shaping is used to establish and maintain a uniform beam waist 26 (see FIG. 2) as the shaped laser beam 18 is scanned to various locations within the stroma 28. Specifically, the apparatus 10 accomplishes this by compensating for those optical aberrations that are introduced by the laser source 12 and, if necessary or desired, compensating for the optical aberrations that are introduced by the optical specimen itself. A more detailed description of an optical assembly for compensating for optical aberrations can be found in U.S. Pat. No. 6,382,797 entitled "Aberration-Free Delivery System" which issued on May 7, 2002 to Bille et al. and is assigned to the same assignee as the present invention. U.S. Pat. No. 6,382,797 is incorporated herein by reference in its entirety.

Continuing now with reference to FIG. 3, it can be seen that the apparatus 10 includes an active mirror 36 which is located on the beam path 38 between the laser source 12 and a beam splitter 40. A suitable active mirror 36 is of a type that is disclosed and claimed by Bille in U.S. Pat. No. 6,220,707 for an invention entitled "Method for Programming an Active Mirror to Mimic a Wavefront," which issued on Apr. 24, 2001 and is assigned to the same assignee as the present invention. U.S. Pat. No. 6,220,707 is incorporated herein by reference in its entirety. Typically, the beam splitter 40 transmits approximately ninety percent (90%) of the light traveling on the beam path 38 toward the eye 22 while diverting ten percent (10%) of the light to a wavefront detector 42. For the apparatus 10, the wavefront detector 42 can be a device known in the pertinent art as a Hartmann-Shack sensor that is capable of analyzing wavefronts.

The light that is transmitted by the beam splitter 40 (i.e. the ninety percent) will continue along the beam path 38 and pass through another beam splitter 44 en route to its incidence on the eye 22. Light reflected from the eye 22 travels back along the beam path 38 and is then diverted by the beam splitter 44 toward the detector 42. It is also shown in FIG. 3 that the wavefront detector 42 is connected via a line 46 with a computer/comparator 48, and that the computer/comparator 48 is connected via a line 50 with the active mirror 36. Additionally, FIG. 3 shows that the computer/comparator 48 is connected via a line 52 with an evaluator 54, and that the evaluator 54 is connected via a line 56 with the laser source 12.

In operation, the laser source 12 directs a source beam 14, which may have an undesirable (e.g. distorted) wavefront, toward the active mirror 36. This source beam 14 is then reflected from the active mirror 36 and a portion of the beam from the active mirror 36 is then reflected to the wavefront detector 42 by the beam splitter 40. The detector 42 is used to identify and define the wavefront of the beam received from the beam splitter 40 and then sends information about the received wavefront to the computer/comparator 48 for analysis. In turn, the computer/comparator 48 will compare this information with a base reference (e.g. a plane wavefront) and generate a signal(s) that is(are) indicative of the differences between the wavefront received at the wavefront detector 42 and the base reference. The signal(s) is (are) then sent via the line 50 to the active mirror 36 for the purposes of programming the active mirror 36 to produce a compensated wavefront. As further shown in FIG. 3, the apparatus 10 can include focusing/scanning optics 58 interposed between the active mirror 36 and eye 22 and controlled by the computer/comparator 48 via a line 60. Thus, the active mirror 36 and focusing/scanning optics 58 cooperate to form and maintain the shaped laser beam 18 having a uniform waist 26 (see FIG. 2) from the source beam 14. Alternatively, some or all of the focusing and scanning functions can be performed by the active mirror 36.

Figure 4:
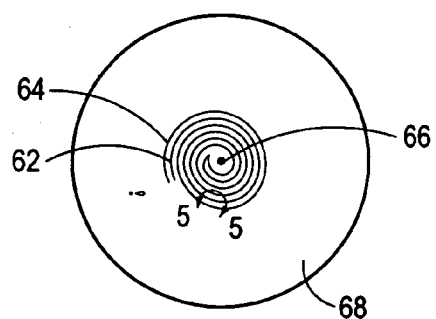
FIG. 4 is a plan view of the cornea of an eye showing exemplary, interlaced spiral scan paths that can be used to minimize heat damage to non-target tissue.
Figure 5:
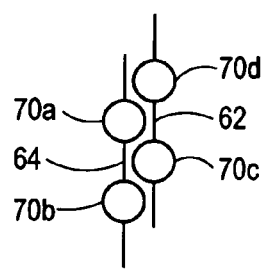
FIG. 5 is a detail view as indicated by arrow 5—5 in FIG. 4 showing exemplary gas bubbles created during a procedure using the spiral scan paths shown in FIG. 4.

Referring now to FIG. 4, an exemplary scanning pattern that can be used to minimize heat damage to non-target tissue during photoablation of target tissue is shown. Specifically, the waist 26 (see FIG. 2) and accordingly the ablation zone 30 can be scanned along two interlaced, spiral paths 62, 64 to minimize heat damage to non-target tissue. In one implementation, the waist 26 and the ablation zone 30 are first scanned outwardly from the corneal center 66 and toward the corneal periphery 68 on spiral path 62. Thereafter, waist 26 and the ablation zone 30 are scanned inwardly in a direction from the corneal periphery 68 and toward the corneal center 66 on spiral path 64. FIG. 5 shows exemplary gas bubbles 70a–d that are created during scanning of the spiral scan paths 62, 64 shown in FIG. 4. As shown, the spiral paths 62, 64 are interlaced providing a spacing between adjacent gas bubbles 70a–d and preventing overlap of adjacent gas bubbles 70a–d that can cause heat damage to non-target tissue.

Figure 6:
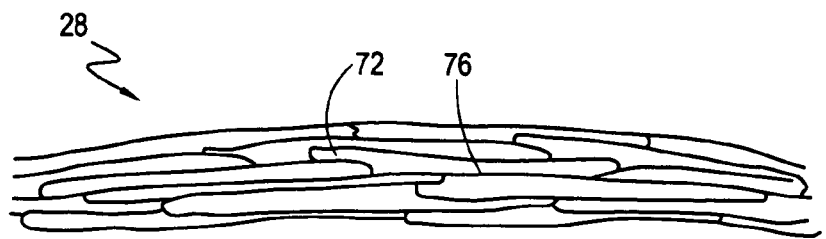
FIG. 6 is an enlarged sectional illustration of two exemplary layers of stromal lamellae in the cornea of an eye.

As best seen with cross-reference now to FIGS. 3 and 6, the apparatus 10 can be used to selectively photoablate target tissue lying inside a lamella 72. As shown in FIG. 3, reflected light 24 from the eye 22 is reflected to the wavefront detector 42 by the beam splitter 44, and for this application can be received by an ellipsometer 74 that is capable of determining the birefringent properties within stromal tissue. For the purposes of the present invention, an ellipsometer of the type disclosed and claimed in U.S. Pat. No. 5,822,035, which issued to Bille for an invention entitled "Ellipsometer," is suitable.

To ablate tissue lying inside a lamella 72, the waist 26 of the shaped laser beam 18 is positioned at a predetermined depth from the anterior surface 34 of the cornea 20 as shown in FIG. 2. In response, a gas bubble is formed at the ablation zone 30. The size of the gas bubble is then measured using the wavefront detector 42 and compared with a reference (e.g. 15 µm) to determine whether ablation has occurred inside a lamella 72 or on an interface between layers of lamellae 76. Specifically, if the response is larger than the reference, the indication is that ablation has occurred on an interface between layers of lamellae 76 and if the response is smaller than the reference, the indication is that ablation has occurred inside a lamella 72.

When the gas bubble indicates that ablation is not occurring inside a lamella 72, the depth of the waist 26 can be altered until the subsequent photoablation occurs inside a lamella 72 (i.e. until a bubble is produced that is smaller than the reference value). Once a bubble is created indicating that photoablation has occurred at a location inside a lamella 72, further photoablation can be accomplished by maintaining the depth of the waist 26 and moving the shaped laser beam 18 to create the desired photoablation pattern.

In addition, once a gas bubble is created indicating that photoablation has occurred at a location inside a lamella 72, the ellipsometer 74 can be used to detect a birefringent condition at the location. Specifically, this birefringent condition results from the orientation of fibrils in the lamella 72. Further, it is known that from layer to layer of lamellae 72 there will be a birefringent change that is manifested as a change in phase of about one half degree. Accordingly, the detection of the birefringent change can indicate a change from one layer of lamellae 72 to another. Consequently, detection of the birefringent change can be used to establish and maintain the ablation zone 30 at a desired depth in the stroma 28.

By photoablating a plurality of stromal lamellae 72 in this manner, the refractive properties of the cornea 20 can be altered. Further, the wavefront detector 42 can be used during the photoablation procedure to track the progress of the corrective procedure. Specifically, the wavefront detector 42 can be used to provide continuously updated information concerning the refractive properties of the cornea 20 to the surgeon during the course of the procedure. This continually changing information allows the surgeon to select the amounts and locations of stromal tissue that must be subsequently altered to obtain the desired shape for the cornea 20. A more detailed discussion regarding the use of wavefront analysis to photoablate inside stromal lamella to alter the refractive properties of the cornea can be found in co-pending U.S. application Ser. No. 09/976,177 entitled "A Device and Method for Performing Refractive Surgery" filed Oct. 12, 2001, the entire contents of which were previously incorporated herein by reference.

In a somewhat similar manner, the apparatus 10 can be used in applications in which the tissue targeted for ablation lies on an interface between layers of lamellae 76. One such application in which the tissue targeted for ablation lies on an interface between layers of lamellae 76 is the creation of a corneal flap that can be peeled away from the remaining stroma to expose stromal tissue for ablation in a LASIK type procedure. For a more detailed discussion regarding the use of wavefront analysis to photoablate on an interface between layers of lamellae to create a corneal flap, see U.S. Pat. No. 6,451,006 entitled "Method for Separating Lamellae" which issued on Sep. 17, 2002 to Bille and is assigned to the same assignee as the present invention. U.S. Pat. No. 6,451,006 is incorporated herein by reference in its entirety.

To ablate tissue on an interface between layers of lamellae 76, the waist 26 of the shaped laser beam 18 is positioned at a predetermined depth from the anterior surface 34 of the cornea 20 as shown in FIG. 2. In response, a gas bubble is formed at the ablation zone 30. The size of the gas bubble is then measured using the wavefront detector 42 and compared with a reference (e.g. 15 µm) to determine whether ablation has occurred inside a lamella 72 or on an interface between layers of lamellae 76.

When the gas bubble indicates that ablation is not occurring on an interface between layers of lamellae 76, the depth of the waist 26 can be altered until the subsequent photoablation occurs on an interface between layers of lamellae 76 (i.e. until a bubble is produced that is larger than the reference value). Once a bubble is created indicating that photoablation has occurred at a location on an interface between layers of lamellae 76, further photoablation can be accomplished by maintaining the depth of the waist 26 and moving the shaped laser beam 18 to create the desired photoablation pattern.

Figure 7:
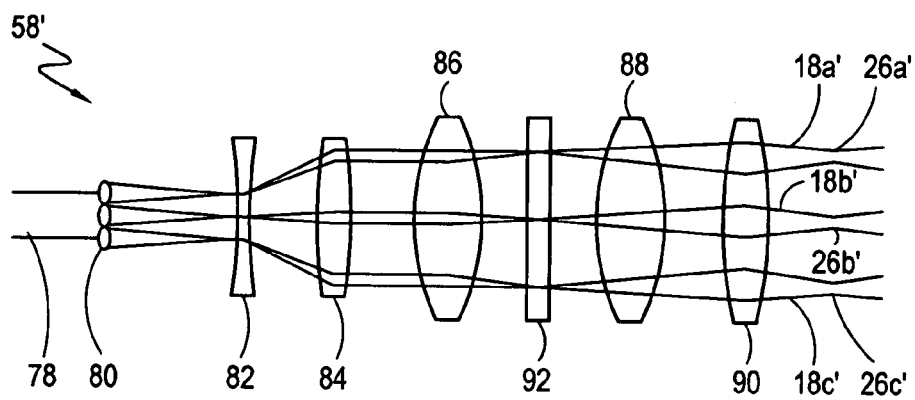
FIG. 7 shows an exemplary optical arrangement for partitioning a main pulsed laser beam into a plurality of beams to allow a plurality of spaced-apart ablation zones to be created simultaneously.

With cross-reference now to FIGS. 3 and 7, another embodiment of the apparatus 10 can be seen wherein the source laser beam 14 is partitioned to allow a plurality of spaced-apart ablation zones 30 (single ablation zone 30 shown in FIG. 2) to be created simultaneously. In greater detail, the beam reflected from the active mirror 36 (designated beam 78 in FIG. 7) can be partitioned, shaped and scanned using the optics 58' shown in FIG. 7, which for this embodiment, constitute the focusing/scanning optics 58 shown in FIG. 3.

In greater detail, the optics 58' includes a lenslet array 80 to partition the beam 78 into a plurality of spaced-apart beams that are directed into a field lens 82 to diverge the beams. From the field lens 82, the diverging beams are directed to a collimating lens 84 to place the beams onto parallel beam paths. Next, the collimated beams are directed to a pair of relay lenses 86, 88 arranged as a telescope to magnify the collimated beams. Once magnified, the beams are directed to a cutting lens 90 to shape the beams and thereby produce a plurality of shaped beams (e.g. seven beams) of which 18a', 18b' and 18c' are shown, with each shaped beam 18a'-c' formed with a respective waist 26a'-c'. Like the lenslet array 80, the cluster of waists 26 is preferably arranged with six waists 26 distributed uniformly around a circle with the seventh waist 26 positioned at the center of the circle. Also shown in FIG. 7, a scanner 92 is provided to move the cluster of waists 26, as a group.

In another embodiment of the apparatus 10, the active mirror 36 can be used in place of the lenslet array 80 and field lens 82. For both embodiments, a plurality of shaped laser beams 18 are produced with each shaped laser beam 18 having a pulse duration and pulse energy sufficient to create a plurality of ablation zones 30 (see FIG. 2), with each ablation zone 30 being created on a respective beam path between the respective beam waist 26 and the optics 58'. For a more detailed discussion regarding the use of optics to partition a beam and then shape and scan the resulting beams to simultaneous photoablate at a plurality of locations, see co-pending U.S. patent application Ser. No. 09/919,627 entitled "Laser Beam Delivery System With Multiple Focal Points" filed Jul. 27, 2001 which is assigned to the same assignee as the present invention. U.S. patent application Ser. No. 09/919,627 is incorporated herein by reference in its entirety.

Figure 8:
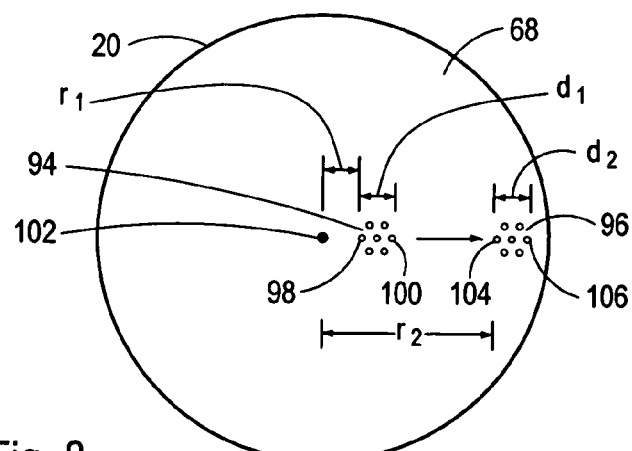
FIG. 8 is a simplified, not to scale, plan view of the cornea of an eye showing exemplary gas bubbles that result from stromal ablation with a plurality of beams.

FIG. 8 shows two bubble clusters 94, 96 that have each been created in response to photoablation with seven spaced-apart beams that have been scanned from a first location (location of cluster 94) to a second location (location of cluster 96). Also shown, cluster 94 includes first bubble 98 corresponding to a first beam waist 26, such as waist 26a in FIG. 7 and a bubble 100 corresponding to a second beam waist 26, such as waist 26c in FIG. 7. As further shown, bubble 98 is spaced from the optical axis 102 of the eye by a radius, $r_1$ and bubble 100 is spaced from bubble 98 by a distance, $d_1$. Also, cluster 96 includes first bubble 104 corresponding to a first beam waist 26, such as waist 26a in FIG. 7 and a bubble 106 corresponding to a second beam waist 26, such as waist 26c in FIG. 7. As further shown, bubble 104 is spaced from the optical axis 102 of the eye by a radius, $r_2$ and bubble 106 is spaced from bubble 104 by a distance, $d_2$. It can be further seen from FIG. 8 that the bubbles 98 and 100 are spaced closer together than the bubble 104, 106 and thus, $d_2<d_1$ with $r_2>r_1$.

Accordingly, FIG. 8 illustrates that the spacing between ablation zones 30 within a cluster 94, 96 can be adjusted in relation to the corneal location where tissue is being ablated. More specifically, for ablation of tissue near the optical axis 102 where heat dissipation is relatively slow, a relatively large spacing between ablation zones 30 within the group of spaced-apart beams can be used to minimize heat damage. On the other hand, for ablation of tissue near the periphery 68 of the cornea 20 where heat dissipation is relatively fast, a relatively small spacing between ablation zones 30 within a cluster 94, 96 can be used.

The use of spaced-apart beams allows a relatively large pattern of tissue to be ablated quickly. For example, a 6.5 mm treatment zone (requiring approximately 400,000 pulses) can be scanned in approximately 3 seconds using seven spaced-apart beams with each beam creating an ablation zone 30 having an approximate diameter $D_{ZONE}$ of approximately 15–20 μm. This corresponds to each beam having 600 fs pulse duration, 6μJ pulse energy, a 10 μm waist diameter and a 10 KHz repetition rate. Thus, an average wavefront correction for a higher order aberration (approximately 1 dpt) or a touchup procedure can be accomplished in less that 10 seconds.

While the particular Method and Apparatus for Intrastromal Refractive Surgery as herein shown and disclosed in detail is fully capable of obtaining the objects and providing the advantages herein before stated, it is to be understood that it is merely illustrative of the presently preferred embodiments of the invention and that no limitations are intended to the details of construction or design herein shown other than as described in the appended claims.

What is claimed is:

1. A method for photoablating stromal tissue, said method comprising the steps of:

providing an optical system;

using said optical system to form a shaped laser beam along a beam path, said laser beam having a waist at a predetermined distance along said beam path from said optical system;

directing said laser beam to position said targeted tissue for ablation along said beam path and to position said waist at non-targeted tissue;

controlling the pulse duration and pulse energy of said laser beam to create an ablation zone along said beam path between said waist and said optical system to photoablate said targeted tissue at said ablation zone while preserving said non-targeted tissue at said waist and to produce a gas bubble in response to photoablation of said stromal tissue at said ablation zone, said gas bubble having a diameter;

comparing said diameter of said gas bubble to a reference value to determine whether said gas bubble is inside a stromal lamella;

using said comparing step to select a subsequent location inside a stromal lamella for photoablation:

moving said waist of said laser beam to ablate stromal tissue at said selected subsequent location; and repeating said directing step and said controlling step to successively reposition said waist at a selected variable distance from a previous waist position.

2. A method as recited in claim 1 wherein said comparing step is accomplished by employing a wavefront detector and a processor.

3. A method as recited in claim 1 wherein said reference value is indicative of a gas bubble in the stroma having a diameter of approximately fifteen microns.

* * * * *